United States Patent [19]

Nordin et al.

[11] 4,185,386
[45] Jan. 29, 1980

[54] HOLDER FOR TURBINE-DRIVEN DENTAL DRILL

[75] Inventors: Elling H. Nordin; Karl O. Sjoman, both of Enköping, Sweden

[73] Assignee: Svedia Dental-Industri Aktiebolag, Sweden

[21] Appl. No.: 721,785

[22] Filed: Sep. 9, 1976

[30] Foreign Application Priority Data

Sep. 19, 1975 [SE] Sweden ................................ 7510533

[51] Int. Cl.² .............................................. A61C 1/12
[52] U.S. Cl. ...................................... 433/82; 433/130
[58] Field of Search ...................... 32/27, 26, DIG. 1

[56] References Cited

U.S. PATENT DOCUMENTS

| | | | |
|---|---|---|---|
| 1,039,420 | 9/1912 | MacDonald | 32/27 |
| 1,216,375 | 2/1917 | Sved | 32/27 |
| 1,356,352 | 10/1920 | Gonzalez | 32/27 |
| 3,163,934 | 1/1965 | Wiseman | 32/27 |
| 3,762,052 | 10/1973 | Melde | 32/27 |

FOREIGN PATENT DOCUMENTS

| | | | |
|---|---|---|---|
| 230847 | 10/1960 | Australia | 32/27 |
| 1098162 | 1/1961 | Fed. Rep. of Germany | 32/27 |
| 2160739 | 6/1973 | Fed. Rep. of Germany | 32/27 |

*Primary Examiner*—Louis G. Mancene
*Assistant Examiner*—John J. Wilson
*Attorney, Agent, or Firm*—Robert E. Burns; Emmanuel J. Lobato; Bruce L. Adams

[57] ABSTRACT

A holder for turbine-driven dental tools such as drills. The holder is made of two-parts comprising an elongated shank and an anglepiece having a head in which is mounted an air-driven turbine for driving the dental tools. Provision is made by a coupling structure for attachably coupling the anglepiece to the shank. A finger-grip sleeve is provided on the coupling structure that allows the holder to be held in position while angularly positioning the holder angularly at set angular positions relative to the sleeve. The operator can thus hold the holder at a desired position and still rotate the anglepiece angularly by rotating the shank about its axis.

4 Claims, 9 Drawing Figures

HOLDER FOR TURBINE-DRIVEN DENTAL DRILL

BACKGROUND OF THE INVENTION

The present invention relates to a holder for turbine-driven dental drills.

The present invention relates to a holder for a turbine driven dental drill, said holder comprising a rod-shaped shaft portion which is arranged at one end for connection to lines for driving to the turbine and providing a cooling medium for the drill, and at its other end merges into an angular piece containing a turbine with a drill connected coaxially thereto, the axis of the drill extending substantially at right angles to the longitudinal direction of the holder.

In dental treatment, the dentist needs in pertinent cases to drill into the teeth of the patient, whereas the drill may need to be directed in different directions depending on the position of the place treated. During continued treatment, the direction of the drill may need to be altered from time to time to obtain the desired form for the tooth surfaces worked on. Drilling in teeth is a precision task which requires accurate guidance of the tool. To achieve this accurate guidance it is necessary for the dentist to support the hand holding the drilling tool in some way. This tool generally comprises a rod-shaped holder terminated at its free end by an angle piece in which the drill is rotatably mounted with its axis substantially at right angles to the longitudinal direction of the holder. To be able to adjust the drill in different directions the dentist must now twist or rotate the drill in his hand. This involves a drawback since the most suitable working position and support for the hand can be difficult or impossible to attain in many cases, if the grip on the drill holder has been altered.

The said drawback has especially made itself felt in using modern turbine driven drills with great removal capacity, which per se enables very effective and rapid machining, whereas large demands are, however, placed on suppleness of the hand in guiding the drill, so that the effective machining possibilities of the tool can be fully utilized.

SUMMARY OF THE INVENTION

The invention relates primarily to providing a holder for a turbine-driven dental drill, eliminating said drawback and giving the dentist the possibility of always gripping the drill holder during treatment in the most suitable hand attitude, while ensuring sufficient support for the hand to enable firm and accurate guidance of the drill.

Accordingly, the invention is characterized by a finger grip sleeve arranged on the drill holder, the finger grip sleeve being rotatable about the holder against the action of a restraining frictional force so that without altering hand attitude the holder can be adjusted for operation in varying rotational positions about its longitudinal axis by holding the sleeve angularly stationary.

The finger grip is suitably made as a rotatable sleeve provided with outer gripping surfaces. This rotatable sleeve is rotatably mounted on the holder, whereby complementary engaging axial splines in the mounting surfaces allow, by means of elastic deformation, stepwise rotation of the rotatable sleeve while retaining a sufficient frictional force for the drill holder not to alter its position relative to the finger grip sleeve, which is kept in an unaltered position during treatment.

In a further advantageous embodiment, the drill holder is made from a shaft portion and an angle piece as separate parts per se, which are rotatably and removably coupled to each other, the rotatable sleeve or finger grip lying between said parts.

The last-mentioned subdivision of the drill holder involves the particular advantage that the angle piece with the turbine accommodated therein can be incorporated in the holder as a separate exchangable part complete with a turbine therein. Modern turbine driven dental drills work at great speed, up to 400,000 rpm, and are usually journalled in ball bearings to ensure sufficiently accurate and stable mounting. Unavoidable wear makes periodic exchange of the turbine necessary, however, this requires special technical knowledge. The rational solution is then to exchange the angle piece with the turbine mounted therein, which is easily done with a drill holder according to the invention.

An especially advantageous embodiment of the invention solves the particular problem which often arises in conjuntion with the cooling system for turbine-driven dental drills. These drills are cooled with the aid of water jets coming from jet canals in the turbine housing and directed towards the drill cutting edge. These canals have a very small cross-section (the diameter is in the order of magnitude of some tenths of a mm), the canals therefore easily are blocked up. Necessary pressure for the cooling liquid is obtained from the pressure medium for the turbine and is preferably dependent on the pressure in the return line. This pressure is normally only insignificantly higher than the ambient atmospheric pressure. By temporary increase of said return pressure there is the possibility of providing a clearing blow-through of the jet canals for the cooling liquid. The required pressure increase is achieved according to the invention in a simple manner by a throttling slide valve in the return line, said slide valve being mounted on the drill holder and can be easily operated as required during treatment in progress.

The invention allows a simple design of the different parts of the drill holder, so that these can for example be manufactured by moulding in metal of plastic.

The invention is described below in the form of an embodiment example while referring to the appended drawing.

DESCRIPTION OF THE PREFERRED EMBODIMENTS

The holder consists of a substantially rod-shaped part, connectable at one end to lines for driving and cooling medium, the other end being shaped into an angle piece with a head accommodating the turbine driving and carrying the drill, the axis of the turbine extending in a transverse direction to the general longitudinal direction of the holder. The angle piece accommodating the turbine with drill extends preferably at a certain angle from the main axis of the holder, so that the drill tip will lie essentially on this main axis. The holder is gripped about the portion situated along its main axis.

In the shown embodiment according to the invention the holder comprises a rod-shaped shank part 1, provided at one end with connecting means 17 for flexible lines arranged for supply of driving and cooling mediums. The driving or working medium usually consists of compressed air, which is supplied and regulated from an unillustrated unit, and the cooling medium usually consists of water also supplied from said unit. The shank part 1 is intended to be gripped by the dentist and is suitably shaped for gripping in the hand an appropriate way. In the example the shank part is shown as a circular truncated cone, for the sake of simplicity, but can preferably be provided with suitably shaped flat or curved gripping surfaces.

Figure 1:
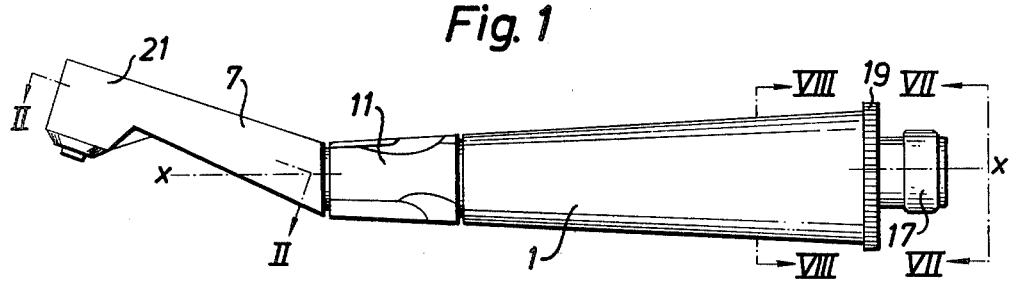
FIG. 1 is a side view of the drill holder according to the invention.
Figure 2:
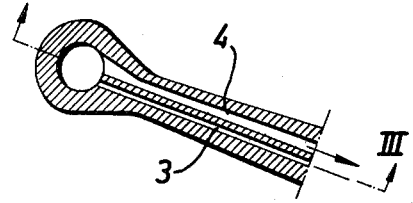
FIG. 2 is a section along the line II—II in FIG. 1.
Figure 3:
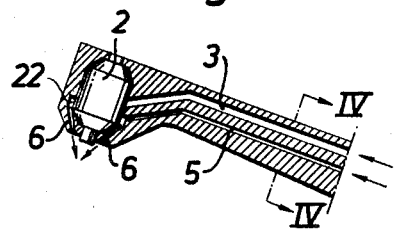
FIG. 3 is a vertical section through the angle piece of the holder on the line III—III in FIG. 2.
Figure 4:
FIG. 4 is a cross-section through the angle piece showing the position of canals for driving medium and cooling medium, on the line IV—IV in FIG. 3.
Figure 5:
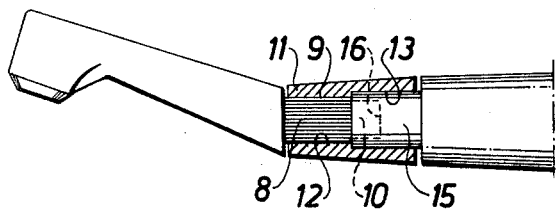
FIG. 5 is a partial view of the holder and shows in more close detail the coupling between the parts of the holder and the mounting of the finger grip.
Figure 6:
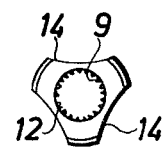
FIG. 6 is an end view of the finger grip formed as a rotatable sleeve.
Figure 7:
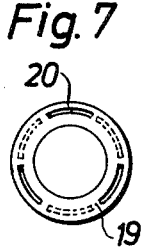
FIG. 7 is an end view of the holder on the line VII—VII in FIG. 1, showing the throttling slide with its openings.
Figure 8:
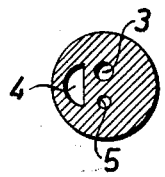
FIG. 8 is a section on the line VIII—VIII in FIG. 1.
Figure 9:
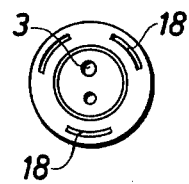
FIG. 9 is an end view of the holder on the line VII—VII in FIG. 1 and shows the holder with the throttling slide removed.

The shank part 1 merges in its forward portion into an angle piece 7 which is nonrotatably connected to the shank part by a coupling device more closely described below. The angle piece 7 is terminated in its end portion by a head 21, accommodating a turbine 2, the axis of which extends at right angles to the main direction of the angle piece 7. As may be seen from FIG. 1, the angle piece extends at a certain angle to the main axis X—X of the holder, whereby the turbine with its drill attachment will lie at such a distance from the main axis X—X that the drill tip will be in the vicinity of said main axis.

Driving medium in the form of compressed air is supplied from the connection 17 through the canal 3 to the turbine 2, whereas the coupling device between the shank portion 1 and the angle piece 7 is so arranged that the canal passes through this coupling without interruption. From the turbine, the used working fluid or driving medium is returned through the return canal 4 parallel to the supply canal 3, passing through the coupling portion between the angle piece and the shank part, whereafter the canal 4 in the rear portion of the shank part 1 is branched out into three outlet openings 18 for release to atmosphere.

Cooling medium in the form of water is supplied through the canal 5 which extends parallel to the canals 3 and 4 and in a similar way passes the coupling portion between the shank part and the angle piece. In the head 21 of the angle piece, the cooling medium canal 5 opens out into an angular canal 22 around the lower portion of the turbine, from which canal the cooling medium departs under pressure through a number of outlet or jet canals 6 directed towards the drill. Necessary pressure for ejecting the cooling liquid is obtained from the pressure medium around the turbine. The flows in said annular canal 22, and part of it is branched off in the direction of the drill together with the cooling medium, although the main portion reflows through the return canal 4 after use in the turbine.

As stated hereinbefore, the drill holder must be turned in varying angular attitudes, about its main axis X—X during the progress of the work and according to the position of the place treated. This requires a readjustment of the hand grip about the holder and affects the ability of supporting the hand in a suitable way in the most advantageous working position. The holder is normally gripped similarly to a pen, for example, whereas its forward portion is embraced by the thumb, index finger and long finger, while the rear portion of the holder rests against the portion of the hand between thumb and index finger. For accurately guiding the drill it is desirable comfortably to be able to support the hand in its normal attitude as far as possible, i.e. without twisting the hand to much. Up to now this has meant altering the whole grip around the holder with a subsequent new grip and supporting position for the hand.

To facilitate the adjustment of the drill holder in varying angular attitudes about its main axis while ensuring substantially unaltered hand position, a rotatable finger grip is arranged according to the invention in the form of a twisting or rotatable sleeve 11 intended to be embraced by the operator's fingers. The twisting sleeve 11 is rotatably mounted on a carrying pin 15 extending from the shank part, and on a carrying pin 8 extending from the angle piece. Both these carrying pins are also provided with coupling means for nonrotatable connection of the angle piece 7 to the shank part 1. The twisting sleeve 11 will thus extend over the coupling portion between the shank part and the angle piece. The carrying pin 15 has a smooth cylindrical journalling surface against which a complementary inner bearing surface 13 of the twisting sleeve engages. On the other hand, the carrying pin 8 on the angle head is provided with longitudinal splines 9 arranged for engagement with complementary splines 9 on the inner bearing surface 12 of the twisting sleeve. The twisting sleeve 11 with its splines is made from elastically deformable material, e.g. a suitable plastic, so that the splines 9 on the pin 8 and on the twisting sleeve 11 can fit each other against resistance on rotation of the sleeve relative to the angle piece and holder. The resistance exercised against rotation of the sleeve is by corresponding dimensioning of the splines, so adjusted that the holder by means of the finger grip or the twisting sleeve 11 can be sufficiently firmly retained in every desired locked position. The splines 9 are placed very close to each other so that rotation of the sleeve in very small steps between each locked position is enabled. By means of this arrangement the dentist has the possibility of turning the remaining part of the holder relative to the sleeve 11 to direct the drill according to need in each case, while retaining unaltered hand attitude and unaltered grip on the twisting sleeve 11.

The twisting sleeve 11 is suitable made with gripping surfaces 14 in the shape of three inwardly curved surfaces intended to be gripped by the said three fingers.

The coupling between the shank part 1 and the angle piece 7 takes place with the help of coupling means of a coupling pin 10 on the angle piece, engaging with a corresponding recess 16 in the carrying pin 15 of the shank part. The coupling device is made with suitable guides for ensuring nonrotatable connection of the parts in a conventional way not more closely described. Respective canals in the shank part and angle piece meet each other via sealing elements provided on the coupling surfaces in a conventional way.

The parts can be kept together in the coupling position by friction adjustment of the coupling pin 10 in the recess 16 or by the aid of further locking means. Since the twisting sleeve 11 extends over the carrying pins 8 and 15, the sleeve contributes in stabilizing the coupling between the shank part and the angle piece.

The sub-division of the holder into a shank part 1 and an angle piece 7 according to the invention brings with it the further advantage that the angle piece and turbine fitted therein can be incorporated in the holder as a complete and easily fitted or removed replacement part. As has been mentioned above the drill and turbine operate at very high revolutions, viz. up to 400,000 rpm. In order to obtain sufficiently rigid guidance of the drill it is preferred to journal the turbine shaft in ball bearings. With the prevalent high revolution speeds, there is unavoidable wear of the bearings after a while, for which reason these bearings and possibly the turbine needs to be replaced. Previously, the entire holder has had to be claimed with this intention, either for arranging the exchange to take place at a specialist workshop or possibly for exchange of necessary parts on the spot. Either alternative involves drawbacks, since the holder in one case must be taken out of use for a certain time, and exchange in the other case has perhaps not taken place with sufficient accuracy, so that the result has not been so successful.

In contra distinction hereto, the invention enables simple exchange of a limited part of the holder, which entails a correspondingly less cost, and it should be particularly noted here that the exchange takes place very quickly and simply. The angle piece has a simple shape and limited size and without problems can be manufactured by moulding in light metal or plastic, wherein inner canals as well as the whole of the outer surface including the splines 9 can be produced during moulding, only insignificant finishing work is required for fitting the turbine with its bearings and immediately adjacent canals, and also possibly the surfaces mating with those on the shank part. It is naturally also possible to combine the shank part with angle pieces of varying shape, for meeting special needs.

The cooling medium is supplied according to the above via the annular canal 22 and the jet canals 6 in the head 21 of the angle piece. These canals 6 are very small, with a diameter of only some tenths of a millimeter. As a result, it can easily happen that small particles in the cooling medium are deposited in the canals 6 causing blockages. As the annular canal 22 is in communication with the return canal 4, the positive pressure in the annular canal is insignificant, and this pressure is not sufficient to remove blockages in the canals 6. To clear the canals it has been previously necessary to use clearing pins or make some special arrangment for increasing the blow-out pressure. As cooling of the drill is an unavoidable necessity, the occurrence of a blockage in the exit canals has meant that the treatment had to be broken off if the cooling medium supply was insufficient. The invention circumvents said drawback by a simple means enabling control of the blow through pressure while also using the holder.

According to the invention, the measure is taken of increasing the pressure in the return canal 4 by constricting the outlet cross-section of the canal. By this pressure increase, the pressure in the annular canal 22 will be sufficient to remove any blockage of the outlet canals 6 occurring in practice. Constriction of the return canal is done with the aid of a rotatable shaped throttling slide or slide valve 19. The throttling slide or slide valve is placed adjacent the outlet openings 18 for the return canal in the rear end of the shank portion, and is provided with openings 20 shaped to correspond to the outlet openings 18. In the example shown, there are three outlet openings 18 and three corresponding openings 20 in the throttling slide, arranged in such a way that the outlet openings 18 in one position of the throttling slide are completely covered, and after twisting the throttling slide 60° they are completely open. The throttling slide 19 is rotatably mounted in a suitable way on the shank part 1 and axially guided so that its inner plane surface glidingly and sealingly engages with the plane end surface of the shank part with the openings 18. The throttling slide is provided with an outer knurled edge serving as a grip for adjusting the slide in a desired pressure position. The slide is normally in the open position so that the openings 18 and 20 lie opposite each other and allow unhindered outlet for the return medium. As required, the ring 19 is turned the necessary amount so that the return pressure increases and the canals 6 are blown clear. In practice, this operation can take place while the holder is in use.

As has been stated above, the twisting sleeve 11 is preferably made from plastic material with sufficient elasticity and strength. The angle piece 7 can be made of similar plastic or alternatively light metal. The shank part 1 can be made from moulded plastic or light metal as desired.

It will be appreciated that the proposed holder construction is economically advantageous, inter alia since the holder is composed of die-cast parts of comparatively simple shape, and can be assembled together without the fitting surfaces of the parts being machined to any great extent. Alternatively it is thus possible to make the coupling surfaces 10, 16 as well as the bearing surfaces on the twisting sleeve 11 and the complementary bearing surfaces on the shank part with sufficient accuracy by die-casting, whereby subsequent machining is made unnecessary. The fitting surfaces for the turbine in the angle piece head 21 can also be die-cast in a finished state. It should be particularly noted that even the turbine 2 can to advantage be produced in metal in a finished state by precision die-casting without subsequent machining, thereby further reducing the cost of manufacture.

What is claimed is:

1. A holder for a turbine-driven dental tool comprising an elonated shank, said shank having means for connection to a working fluid source for driving a turbine and to a source of cooling fluid for flow axially in said shank, a mounting pin on an end of said shank and having an axial bore on an end thereof, a finger-grip sleeve circumferentially of said mounting pin relatively rotatable thereto and extending axially from said end of said mounting pin, said sleeve having deformable internal axial splines, an exchangeable anglepiece removably mounted on said shank, said anglepiece having a coupling pin in said bore for non-rotation therein with resistance for holding the anglepiece in a set angular position, said coupling pin having axial splines received in said finger-grip sleeve and complementary with the splines on said finger-grip sleeve, and said deformable splines being deformable for allowing rotation of the splined coupling pin incrementally in said finger-grip sleeve and thereby allowing positioning said anglepiece at set angular positions upon manual rotation of said shank while said fingergrip sleeve is held manually angularly stationary.

2. A holder for a turbine-driven dental tool according to claim 1, in which said anglepiece comprises a fluid-driven turbine, means for mounting a dental tool thereon for driving by said turbine, and said anglepiece having passages for said working fluid for driving said turbine, and having passages for said cooling fluid for cooling said tool.

3. A holder for a turbine-driven dental tool according to claim 2, including a throttling valve for varying the pressure of said cooling fluid.

4. A holder for a turbine-driven dental tool according to claim 3, in which said throttling valve is a rotatable slide valve mounted on said shank.

* * * * *